United States Patent
Tanaka et al.

(10) Patent No.: US 11,123,320 B2
(45) Date of Patent: Sep. 21, 2021

(54) PROPHYLACTIC OR THERAPEUTIC AGENT FOR HYPERACIIVE BLADDER

(71) Applicants: SBI PHARMACEUTICALS CO., LTD., Tokyo (JP); NATIONAL UNIVERSITY CORPORATION KOCHI UNIVERSITY, Kochi (JP)

(72) Inventors: Tohru Tanaka, Tokyo (JP); Kiwamu Takahashi, Tokyo (JP); Keiji Inoue, Kochi (JP); Motoaki Saito, Kochi (JP); Masayuki Tsuda, Kochi (JP); Hideo Fukuhara, Kochi (JP); Takahira Kuno, Kochi (JP); Shogo Shimizu, Kochi (JP)

(73) Assignees: SBI PHARMACEUTICALS, CO., LTD., Tokyo (JP); NATIONAL UNIVERSITY CORPORATION KOCHI UNIVERSITY, Kochi (JP)

( * ) Notice: Subject to any disclaimer, the term of this patent is extended or adjusted under 35 U.S.C. 154(b) by 63 days.

(21) Appl. No.: 16/613,011

(22) PCT Filed: May 21, 2018

(86) PCT No.: PCT/JP2018/019482
§ 371 (c)(1),
(2) Date: Nov. 12, 2019

(87) PCT Pub. No.: WO2018/221291
PCT Pub. Date: Dec. 6, 2018

(65) Prior Publication Data
US 2020/0163917 A1 May 28, 2020

(30) Foreign Application Priority Data

May 31, 2017 (JP) .............................. JP2017-107367

(51) Int. Cl.
*A61K 31/197* (2006.01)
*A61P 13/10* (2006.01)
*A61K 31/295* (2006.01)

(52) U.S. Cl.
CPC .......... *A61K 31/197* (2013.01); *A61K 31/295* (2013.01); *A61P 13/10* (2018.01)

(58) Field of Classification Search
None
See application file for complete search history.

(56) References Cited

U.S. PATENT DOCUMENTS

| 6,034,267 | A | 3/2000 | Gierskcky et al. |
| 6,559,183 | B1 * | 5/2003 | Schmid .................. A61P 35/00 514/561 |
| 8,575,197 | B2 * | 11/2013 | Kai ...................... C07D 409/14 514/333 |
| 2006/0115540 | A1 | 6/2006 | Toshiyuki et al. |
| 2010/0120916 | A1 | 5/2010 | Toshihiko et al. |
| 2011/0196033 | A1 | 8/2011 | Tohru |
| 2017/0189443 | A1 * | 7/2017 | Parsons .................. A61P 13/10 |

FOREIGN PATENT DOCUMENTS

| JP | 11501914 | 2/1999 |
| JP | 2008255059 | 10/2008 |
| JP | 2013216593 | 10/2013 |
| WO | 2004/041276 | 5/2004 |
| WO | 2010/050179 | 5/2010 |

OTHER PUBLICATIONS

Miyake et al., "A prospective study of oral 5-aminolevulinic acid to prevent adverse events in patients with localized prostate cancer . . . brachytherapy: Protocol ofthe AMBER study", 2020, Contemporary Clinical Trials Communications, vol. 19, pp. 1-7. (doi.org/10.1016/j.conctc.2020.100593) (Year: 2020).*

Mayo Clinic, "Overactive bladder", 2020, pp. 1-7. (https://www.mayoclinic.org/diseases-conditions/overactive-bladder/diagnosis-treatment/drc-20355721?p=1) (Year: 2020).*

International Search Report and Written Opinion English Translation corresponding to International Patent Application No. PCT/JP2018/019482, dated Jun. 19, 2018, 10 pages.

Chang, S.-C. et al. "Photodynamic therapy of rat bladder and urethra: evaluation of urinary and reproductive function after inducing protoporphyrin IX with 5-aminolaevulinic acid" BJU International, 85:747-753 2000.

Extended European Search Report corresponding to European patent application No. 18809087.2, dated Feb. 1, 2021, 7 pages.

Nishio et al. "5-Aminolevulinic acid combined with ferrous iron enhances the expression of heme oxygenase-1" International Immunopharmacology, 19:300-307 2014.

* cited by examiner

Primary Examiner — My-Chau T. Tran
(74) Attorney, Agent, or Firm — Myers Bigel, P.A.

(57) ABSTRACT

Various side effects are reported for existing overactive bladder therapeutic drugs, and prophylactic or therapeutic agents for overactive bladder without side effects have been eagerly desired. The present invention provides a prophylactic or therapeutic agent for overactive bladder that comprises 5-aminolevulinic acids (ALAs) as the active ingredient.

11 Claims, 10 Drawing Sheets

PROPHYLACTIC OR THERAPEUTIC AGENT FOR HYPERACIIVE BLADDER

STATEMENT OF PRIORITY

This application is a 35 USC. § 371 national phase application of International Application Serial No. PCT/JP2018/019482, filed May 21, 2018, which claims the benefit, under 35 U.S.C. § 119 (a) of Japanese Patent Application No. 2017-107367, filed May 31, 2017, the entire contents of each of which are incorporated by reference herein.

TECHNICAL FIELD

The present invention relates to a pharmaceutical composition for preventing or treating overactive bladder.

BACKGROUND ART

Overactive bladder is a symptom syndrome which involves urinary urgency as the obligatory symptom and may be accompanied by nocturia or frequent urination. Here, urinary urgency is "a suddenly occurring, unbearably strong micturition of which the difference from ordinary micturition is difficult to describe," and the pathophysiology or pathogenic mechanism thereof has not been elucidated. Moreover, it is known that one out of eight men and women aged 40 or older has a symptom of overactive bladder.

Anticholinergic agents such as propiverine hydrochloride and oxybutynin hydrochloride are mainly employed as therapeutic agents for overactive bladder. Anticholinergic agents inhibit the effect of acetylcholine to enhance the parasympathetic nerve, thereby inhibiting the diuretic effect. Moreover, in recent years, β3 adrenaline receptor agonist is sometimes employed as a therapeutic agent for overactive bladder that has an action mechanism different from anticholinergic agents (Patent Literature 1). In contrast to said anticholinergic agent, β3 adrenaline receptor agonist is known as something that enhances the β3 adrenaline receptor present in the bladder, and in turn the sympathetic nerve.

CITATION LIST

[Patent Literature 1] WO2004/041276

SUMMARY OF THE INVENTION

Problems to be Solved by the Invention

Said anticholinergic agents have reported side effects such as excretion disorder and dry mouth. Moreover, β3 adrenaline receptor agonists also have reported side effects such as mainly dry mouth, constipation, rash, and urticaria. For this reason, giving consideration to improvement of QOL for overactive bladder patients, production of prophylactic/improvement agents for overactive bladder without side effects has been eagerly desired.

Means for Solving the Problems

As a result of devoted search by the present inventors for compounds that have the possibility to become prophylactic/improvement agents for overactive bladder without side effects, it was surprisingly found that 5-aminolevulinic acids (also referred to herein as "ALAs") have an effect of improving overactive bladder, thereby coming to complete the present invention.

5-aminolevulinic acid (also referred to herein as "ALA") is a type of natural amino acid comprised in vivo that exists widely in animals or plants or fungi. ALA is known to be highly safe for the living body, and its use as a photosensitizer in photodynamic therapy, a plant growth regulator, an herbicide, an infection therapy for fish microbial pathogens and parasites, a pig grown promoter, and the like are known. However, there is no knowledge thus far regarding the effect of ALA against overactive bladder.

In other words, in one embodiment, the present invention relates to a pharmaceutical composition for use in prevention or treatment of overactive bladder comprising the compound shown by the following Formula (I):

[Chemical Formula 1]

$$R^1-NHCH_2COCH_2CH_2COOR^2 \quad (I)$$

(wherein $R^1$ represents a hydrogen atom or an acyl group, and $R^1$ represents a hydrogen atom, a linear or branched alkyl group, a cycloalkyl group, an aryl group, or an aralkyl group) or a salt thereof.

Moreover, in one embodiment, the present invention is characterized in that said overactive bladder is overactive bladder showing a symptom of frequent urination.

Moreover, in one embodiment, the present invention is characterized in that $R^1$ is selected from the group consisting of a hydrogen atom, an alkanoyl group having 1-8 carbons, and an aroyl group having 7-14 carbons, and $R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

Moreover, in one embodiment, the present invention is characterized in that $R^1$ and $R^2$ are hydrogen atoms.

Moreover, in one embodiment, the present invention is characterized in that it further contains one or more types of metal-containing compounds.

Moreover, in one embodiment, the present invention is characterized in that the metal-containing compound is a compound containing iron, magnesium, zinc, nickel, vanadium, copper, chromium, molybdenum, or cobalt.

Moreover, in one embodiment, the present invention is characterized in that the metal-containing compound is a compound containing iron, magnesium, or zinc.

Moreover, in one embodiment, the present invention is characterized in that the metal-containing compound is a compound containing iron.

Moreover, in one embodiment, the present invention is characterized in that said compound containing iron is sodium ferrous citrate.

Another embodiment of the present invention relates to the use of the compound shown by the following Formula (I):

[Chemical Formula 2]

$$R^1-NHCH_2COCH_2CH_2COOR^2 \quad (I)$$

(wherein $R^1$ represents a hydrogen atom or an acyl group, and $R^2$ represents a hydrogen atom, a linear or branched alkyl group, a cycloalkyl group, an aryl group, or an aralkyl group) or a salt thereof for producing a prophylactic or therapeutic agent for overactive bladder.

Another embodiment of the present invention relates to a method for preventing or treating overactive bladder comprising a step of administering to a subject a therapeutically effective amount of the compound shown by the following Formula (I):

[Chemical Formula 3]

$$R^1-NHCH_2COCH_2CH_2COOR^2 \quad (I)$$

(wherein $R^1$ represents a hydrogen atom or an acyl group, and $R^2$ represents a hydrogen atom, a linear or branched alkyl group, a cycloalkyl group, an aryl group, or an aralkyl group) or a salt thereof.

Note that an invention of a combination of one or more characteristics of the present invention described above is also encompassed by the scope of the present invention.

DESCRIPTION OF EMBODIMENTS

The present invention relates to a pharmaceutical composition for preventing or treating overactive bladder. An "overactive bladder" herein means a symptom syndrome which involves urinary urgency as the obligatory symptom and may be accompanied by frequent urination, nocturia, and urge urinary incontinence. In other words, a symptom without incontinence despite frequent urination/urinary urgency is also included in the overactive bladder herein.

Note that "frequent urination" as used herein is one of the main symptoms of overactive bladder, and refers to a symptom where for example there are eight or more micturition desires from wake-up to bedtime, or there are one or more micturition desires during sleep.

ALAs as used herein refers to an ALA or a derivative thereof, or salts thereof.

An ALA as used herein means 5-aminolevulinic acid. ALA is also referred to as δ-aminolevulinic acid, and is a type of amino acid.

The compound shown by the following Formula (I) can be exemplified as an example of an ALA derivative. In Formula (I), $R^1$ represents a hydrogen atom or an acyl group, and $R^2$ represents a hydrogen atom, a linear or branched alkyl group, a cycloalkyl group, an aryl group, or an aralkyl group. Note that in Formula (I), ALA corresponds to when $R^1$ and $R^2$ are hydrogen atoms.

[Chemical Formula 4]

$$R^1-NHCH_2COCH_2CH_2COOR^2 \quad (I)$$

ALAs may act as an active ingredient in vivo in the form of the ALA of Formula (I) or a derivative thereof, and can also be administered as a prodrug (precursor) that is degraded by an in vivo enzyme.

The acyl group in $R^1$ of Formula (I) can include a linear or branched alkanoyl group having 1-8 carbons such as formyl, acetyl, propionyl, butyryl, isobutyryl, valeryl, isovaleryl, pivaloyl, hexanoyl, octanoyl, and benzylcarbonyl groups, or an aroyl group having 7-14 carbons such as benzoyl, 1-naphthoyl, and 2-naphthoyl groups.

The alkyl group in $R^2$ of Formula (I) can include a linear or branched alkyl group having 1-8 carbons such as methyl, ethyl, propyl, isopropyl, butyl, isobutyl, sec-butyl, tert-butyl, pentyl, isopentyl, neopentyl, hexyl, heptyl, and octyl groups.

The cycloalkyl group in $R^2$ of Formula (I) can include a cycloalkyl group having 3-8 carbons which may be saturated or have partially unsaturated bonds, such as cyclopropyl, cyclobutyl, cyclopentyl, cyclohexyl, cycloheptyl, cyclooctyl, cyclododecyl, and 1-cyclohexenyl groups.

The aryl group in $R^2$ of Formula (I) can include an aryl group having 6-14 carbons such as phenyl, naphthyl, anthryl, and phenanthryl groups.

The aralkyl group in $R^2$ of Formula (I) can be exemplified with the same aryl groups as above as the aryl moiety and the same alkyl groups as the above as the alkyl moiety, and can specifically include an aralkyl group having 7-15 carbons such as benzyl, phenethyl, phenylpropyl, phenylbutyl, benzhydryl, trityl, naphthylmethyl, and naphthylethyl groups.

Preferred ALA derivatives include compounds where $R^1$ is a formyl group, an acetyl group, a propionyl group, a butyryl group, and the like. Moreover, preferred ALA derivatives also include compounds where the above $R^2$ is a methyl group, an ethyl group, a propyl group, a butyl group, a pentyl group, and the like. Moreover, preferred ALA derivatives also include compounds where the combination of the above $R^1$ and $R^2$ is each combination of (formyl and methyl), (acetyl and methyl), (propionyl and methyl), (butyryl and methyl), (formyl and ethyl), (acetyl and ethyl), (propionyl and ethyl), and (butyryl and ethyl).

Among ALAs, a salt of ALA or a derivative thereof can include a pharmaceutically acceptable acid addition salt, a metal salt, an ammonium salt, an organic amine addition salt, and the like. Acid addition salts can be exemplified by e.g. each of inorganic acid salts such as a hydrochloride salt, a hydrobromide salt, a hydroiodide salt, a phosphate salt, a nitrate salt, and a sulfate salt, and each of organic acid addition salts such as a formate salt, an acetate salt, a propionate salt, a toluenesulfate salt, a succinate salt, an oxalate salt, a lactate salt, a tartrate salt, a glycolate salt, a methanesulfonate salt, a butyrate salt, a valerate salt, a citrate salt, a fumarate salt, a maleate salt, and a malate salt. Metal salts can be exemplified by each of alkali metal salts such as a lithium salt, a sodium salt, and a potassium salt, each of alkaline earth metal salts such as a magnesium salt and a calcium salt, and each of metal salts such as aluminum and zinc. Ammonium salts can be exemplified by e.g. ammonium salts and alkyl ammonium salts such as a tetramethylammonium salt. Organic amine salts can be exemplified by each of salts such as a triethylamine salt, a piperidine salt, a morpholine salt, and a toluidine salt. Note that these salts can also be employed as a solution at the time of use.

Among the above ALAs, the most favorable are ALA and various esters such as an ALA methyl ester, an ALA ethyl ester, an ALA propyl ester, an ALA butyl ester, and an ALA pentyl ester, as well as hydrochloride salts, phosphate salts, and sulfate salts thereof. In particular, ALA hydrochloride salts and ALA phosphate salts can be exemplified as particularly favorable.

The above ALAs can be manufactured by e.g. well-known methods such as chemical synthesis, production by microorganisms, and production by enzymes. Moreover, the above ALAs may also form a hydrate or a solvate, and ALAs can be employed alone or in an appropriate combination of two or more.

When the above ALAs are to be prepared as an aqueous solution, attention must be paid so that the aqueous solution will not become alkaline in order to prevent degradation of ALAs. In the case it becomes alkaline, degradation can be prevented by removing oxygen.

In one embodiment, the pharmaceutical composition of the present invention may further contain one or more types of metal-containing compounds. The metal portion of such metal-containing compound can include iron, magnesium, zinc, nickel, vanadium, cobalt, copper, chromium, molybdenum, and the like. In a preferred embodiment, the metal portion of the metal-containing compound is preferably iron, magnesium, or zinc, in particular iron.

The iron compound that may be employed in the present invention may be an organic salt or an inorganic salt. Inorganic salts can include ferric chloride, iron sesquioxide, iron sulfate, and ferrous pyrophosphate. Organic salts can include carboxylic salts such as a hydroxycarboxylic salt, citrate salts such as ferrous citrate, iron sodium citrate, sodium ferrous citrate (SFC), and iron ammonium citrate, organic acid salts such as ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminepentaacetate, iron sodium dicarboxymethylglutamate, iron ammonium dicarboxymethylglutamate, ferrous fumarate, iron acetate, iron oxalate, ferrous succinate, and iron sodium succinate citrate, as well as triethylenetetramine iron, lactoferrin iron, transferrin iron, sodium iron chlorophyllin, ferritin iron, saccharated iron oxide, and ferrous glycine sulfate.

The magnesium compound that may be employed in the present invention can include magnesium citrate, magnesium benzoate, magnesium acetate, magnesium oxide, magnesium chloride, magnesium hydroxide, magnesium carbonate, magnesium sulfate, magnesium silicate, magnesium nitrate, magnesium diammonium diethylenetriaminepentaacetate, magnesium disodium ethylenediaminetetraacetate, and magnesium protoporphyrin.

The zinc compound that may be employed in the present invention can include zinc chloride, zinc oxide, zinc nitrate, zinc carbonate, zinc sulfate, zinc diammonium diethylenetriaminepentaacetate, zinc disodium ethylenediaminetetraacetate, zinc protoporphyrin, and zinc-containing yeast.

The dosage of the metal-containing compound to a subject may be 0-100 folds by molar ratio to the dosage of ALA to a subject, desirably 0.01-10 folds, and more desirably 0.1-8 folds.

ALAS and the metal-containing compound contained in the pharmaceutical composition of the present invention can be administered as a composition comprising ALAs and the metal-containing compound or each can be administered alone, although it is preferred that even when administering each alone, they are administered at the same time. Same time here means not only administering simultaneously, but also, even if not simultaneously, administering without substantial interval between each other so that the administration of ALAS and the metal-containing compound can exert additive effect, preferably synergistic effect.

The administration route of ALAs and the metal-containing compound in the present invention is not limited, and may be systemic administration or local administration. Administration routes can include, for example, oral administration including sublingual administration, or parenteral administration such as inhalation administration, direct administration into the target tissue or organ via a catheter, intravenous administration including infusion, transdermal administration by e.g. patches, suppository, or administration by forced enteral nutrition employing nasogastric tube, nasointestinal tube, gastrostomy tube, or enterostomy tube. Moreover, as described above, ALAs and the metal-containing compound may be administered from separate routes.

The dosage form of ALAs, metal-containing compound, or a formulation of a combination thereof employed in the present invention may be appropriately determined depending on the said administration route, and can include, but is not limited to, injections, infusions, tablets, capsules, fine granules, powders, liquids, solutions dissolved in syrups etc., patches, suppositories, and the like.

Other optional ingredients such as medicinal ingredients, nutrients, and carriers can be added as necessary to the pharmaceutical composition according to the present invention. For example, as optional ingredients, various compounding ingredients for preparation of drugs such as pharmaceutically acceptable ordinary carriers e.g. crystalline cellulose, gelatin, lactose, starch, magnesium stearate, talc, vegetable and animal fat, oil, gum, and polyalkylene glycol, binders, stabilizers, solvents, dispersion mediums, expanders, excipients, diluents, pH buffers, disintegrants, solubilizers, solubilizers, and isotonic agents can be added.

The administration frequency or duration of the pharmaceutical composition of the present invention to a subject can be appropriately determined by those skilled in the art (such as a physician) in light of the symptoms or conditions of the subject etc.

The terms used herein, except for those that are particularly defined, are employed for describing particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, and shall not be construed as being limited to the Examples described herein.

EXAMPLES

Example 1 (Effect of Increasing Single Urination Amount Etc. by ALA)

Experimental Group

Twelve weeks old male SHR (spontaneously hypertension rata) were employed as experimental rats, and the experimental groups were divided into groups I-III by ALA administration conditions below. For experimental group II, ALA and sodium ferrous citrate were orally administered on experiment start day. The dosage of ALA was set at 10 mg/kg of body weight and sodium ferrous citrate was set at 15.7 mg/kg of body weight. On the other hand, for experimental group III, ALA was set at 100 mg/kg of body weight and sodium ferrous citrate was set at 157 mg/kg of body weight. Note that for control group I, saline only at an amount equal to ALA was administered instead of ALA and sodium ferrous citrate.

ALA Administration Conditions

For control group I, saline was orally administered every day from experiment start day (12 weeks old) to week 6 (18 weeks old).

For experimental groups II and III, ALA and sodium ferrous citrate was orally administered every day from experiment start day (12 weeks old) to week 6 (18 weeks old).

Method of Measuring Urination Kinetics

For each experimental group, urination kinetics measurement with a metabolic cage was performed. Specifically, measurements were performed at 12 weeks old (before ALA administration) and at 18 weeks old (after ALA administration) to measure single urination amount, 24-hour urination amount, and water drinking amount. Here, the method based on Yono et al., *Life Sci.* 2007 Jun. 27; 81(3):218-222 (non-anesthetized, unrestrained, and day-and-night continuous measurement method of mouse urination function) was adopted as the measurement method with a metabolic cage. Note that before measurement of urination kinetics, body weight, blood pressure, and heart rate were measured as a caution in addition to the urination amount and water drinking amount. Moreover, when measuring urination kinetics, total number of urination was also measured.

Results

Figure 1:
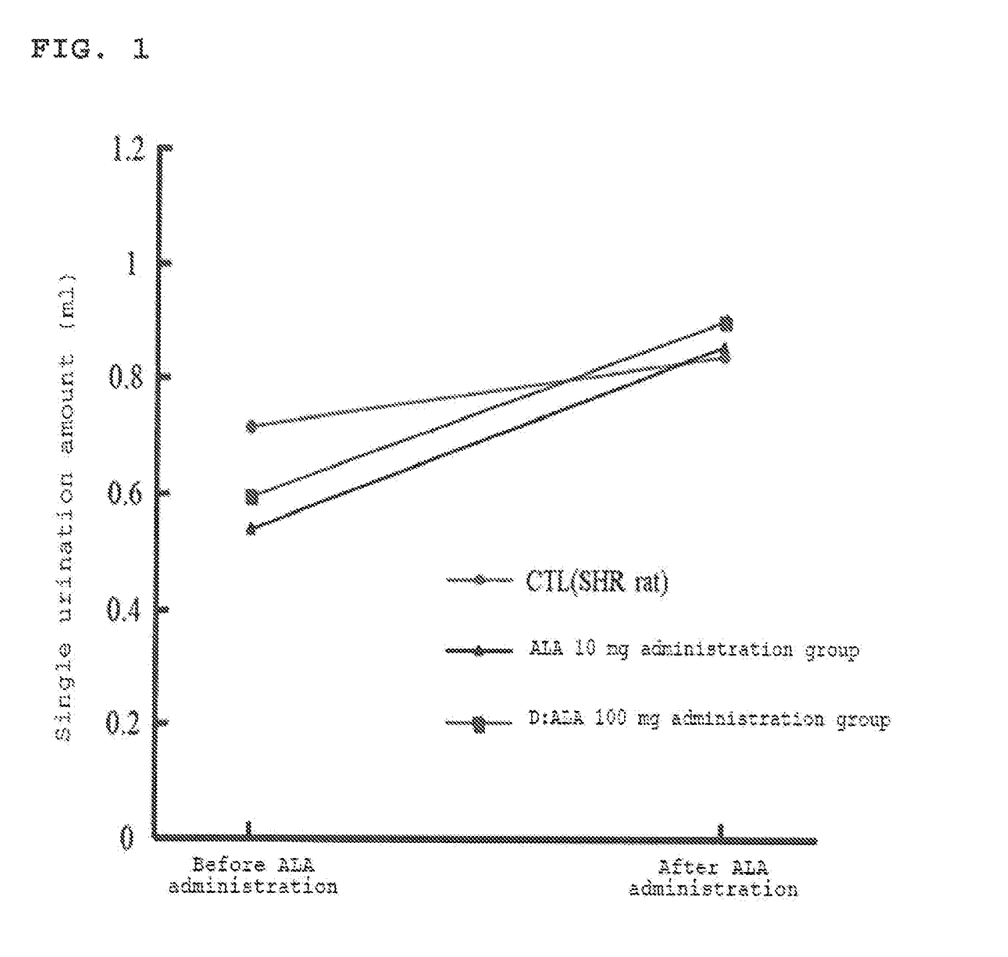
FIG. 1 is a graph showing the single urination amount in the control group and each experimental group.
Figure 2:
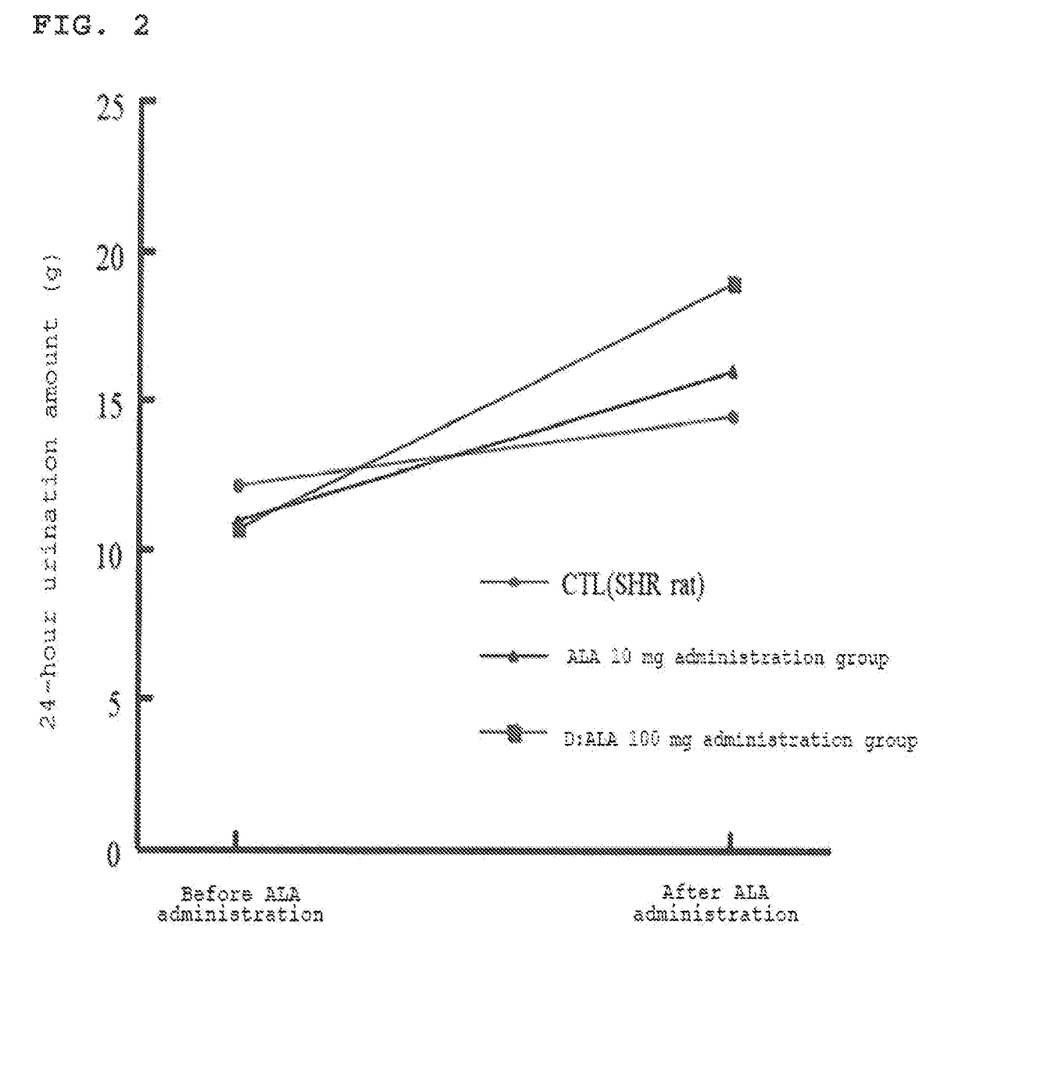
FIG. 2 is a graph showing the 24-hour urination amount in the control group and each experimental group.
Figure 3:
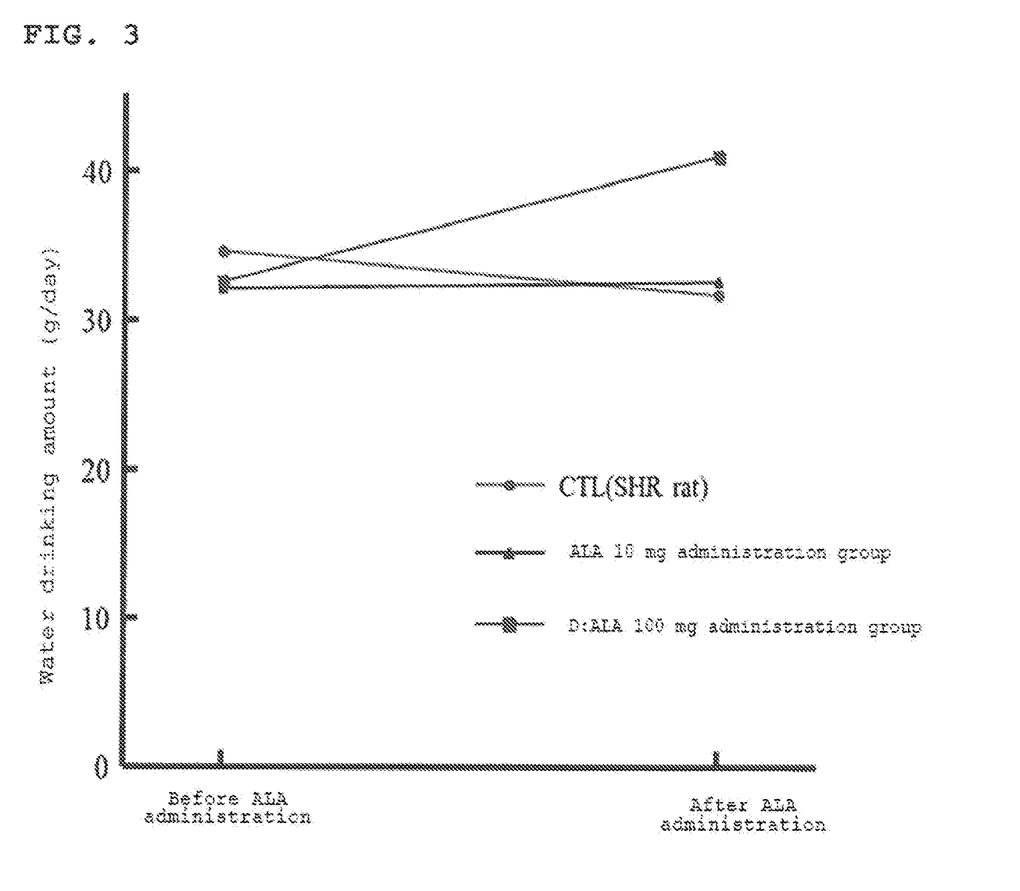
FIG. 3 is a graph showing the 24-hour water drinking amount in the control group and each experimental group.

Results are shown in FIGS. 1-3. FIG. 1 shows the results of single urination amount for each experimental group, where the vertical axis shows the urination amount and the horizontal axis shows the presence or absence of ALA administration. As apparent from FIG. 1, increase in single urination amount (approximately 30%) by ALA administration compared to the control group was confirmed.

Moreover, FIG. 2 shows the results of 24-hour urination amount for each experimental group, where the vertical axis shows the urination amount and the horizontal axis shows the presence or absence of ALA administration. As apparent from FIG. 2, increase in 24-hour urination amount by ALA administration compared to the control group was confirmed.

Further, FIG. 3 shows the result of 24-hour water drinking amount for each experimental group, where the vertical axis shows the water drinking amount and the horizontal axis shows the presence or absence of ALA administration. As apparent from FIG. 3, increase in water drinking amount by ALA administration was confirmed.

Here, in general, there is no difference in bladder capacity for overactive bladder compared to without overactive bladder. For this reason, since increase in single urination amount, 24-hour urination amount, and water drinking amount were confirmed for overactive bladder model rats, it is thought that ALA acted on the adjustment of bladder blood flow and contributed to the increase in bladder urine storage volume. Accordingly, measurement of intravesical pressure was performed in order to confirm the change in bladder blood flow by ALA.

Example 2 (Effect of Urination Duration Extension by ALA)

Cystometry

After said method of measuring urination kinetics, cystometry was performed according to the procedure below. Note that cystometry verifies the overactive status of the detrusor muscle, and is established as a method for examining overactive bladder.

(1) 18 weeks old male SHR/Hos rats and Wistar/ST rat are subjected to general anesthesia by urethane (1.0 g/kg, i.p.).
(2) Each rat is laid down and the extremities are fixed with packaging tape. Laparotomy is then performed, and the bladder is pressed to allow urination. Absorbent cotton with saline is placed on top to prevent drying and left for 30 minutes.
(3) A catheter for cystometry is inserted into the bladder of each rat.

Here, the catheter is joined to a three-way stopcock, and one end is connected to a syringe pump to continuously infuse saline into the bladder at a constant speed (12 ml/hr). The other end is connected to a pressure transducer to monitor and amplify with a pressure amplifier, and incorporated into a personal computer via Powerlab system for recording.

(* PowerLab (16 ch high-speed PowerLab system): PowerLab/16SP model ML 795, ADI (ADInstruments), USA)
(4) Saline is then infused and left for about 30 minutes until stable.
(5) Watch the wave form to collect single urine into a 1.5 ml tube, and the weight of urine is measured.
(6) Residual urine of each rat is collected and the amount is measured.
(7) Peaks at similar interval and height are consecutively taken 6 times (about 1 hour).

Results

Figure 4:
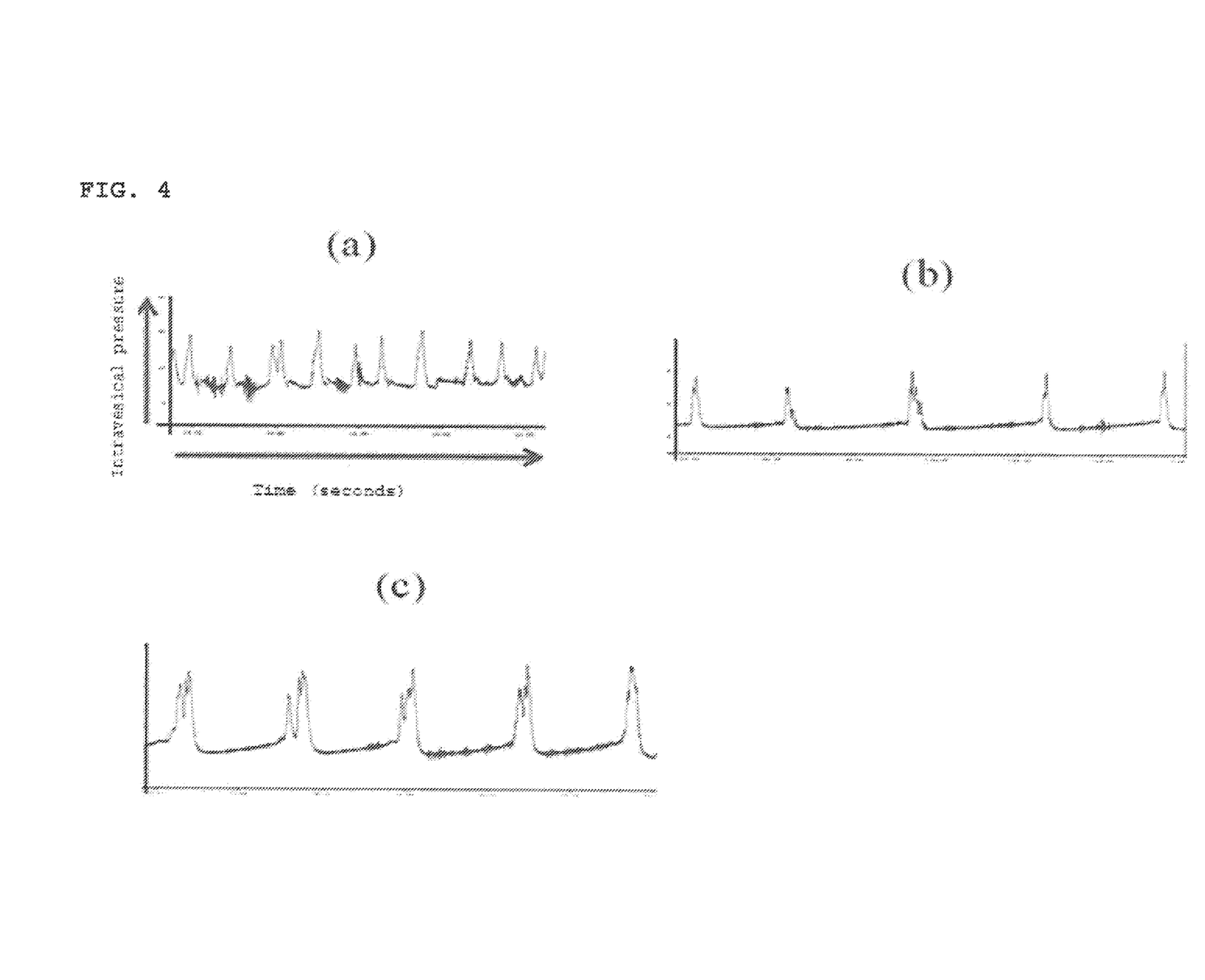
FIG. 4 is a graph showing the active status of the detrusor muscle in the control group and each experimental group.
Figure 5:
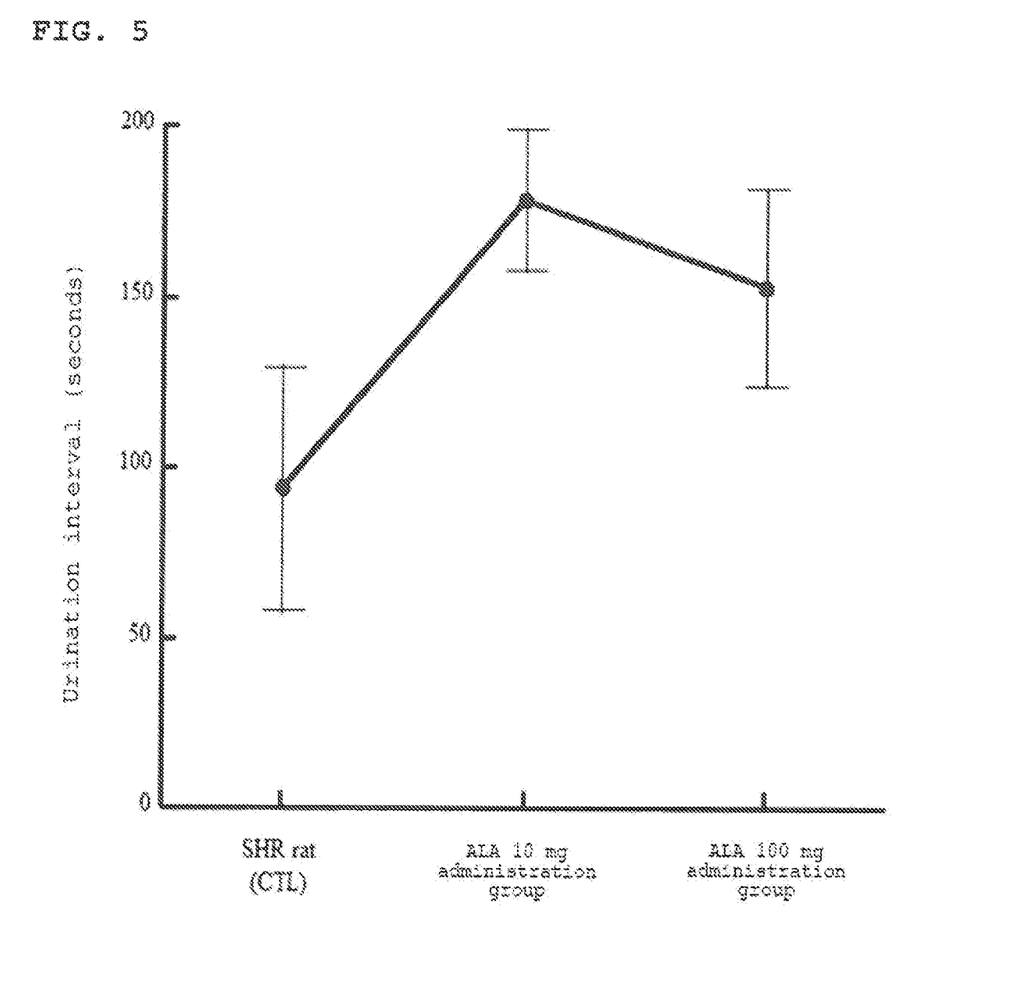
FIG. 5 is a graph that compares the urination interval (seconds) in the control group and each experimental group.

Results are shown in FIGS. 4 and 5. In FIG. 4, (a) shows the result of the control group I, (b) shows the result of experimental group II, and (c) shows the result of experimental group III. In each graph, the vertical axis shows the intravesical pressure and the horizontal axis shows time (seconds). Moreover, FIG. 5 is a transformation of the graph shown in FIG. 4 based on the urination interval (seconds). As apparent from FIGS. 4 and 5, by administering ALA, extension of urination interval was confirmed compared to the group without administration of ALA. From this result, it is thought that the bladder that had contracted due to overactive bladder was expanded by administering ALA, thus increasing the urine storage volume in the bladder.

Example 3 (Effect of Improving Bladder Blood Flow by ALA)

Method

After said cystometry, bladder blood flow measurement (hydrogen clearance method) was performed according to the procedures below.
(1) A silver chloride plate which is an indifferent electrode is buried under the precordium of each rat.

(2) Wire platinum electrodes are incised into the bladder wall (three places in the bladder wall, data is collected 3 times each).
(3) Blood flow is measured using UH-METER.

Specifically, a hydrogen tank is opened to 0.3 L/min, and 100% hydrogen is directly inhaled with a funnel. Hydrogen is given until peaked, and hydrogen clearance curve is measured with the PowerLab system. The timepoint when the hydrogen clearance curve begins to drop is set at 0 second, and recording was performed for about 180 seconds.
(4) The blood flow amount was calculated from the regression curve.

* Half-life ($T\frac{1}{2}$) is determined from the regression curve $Y=B-AX$.

Blood flow amount=$69.3/T\frac{1}{2}$ (ml/min/100 g)

(* PowerLab (16 ch high-speed PowerLab system): PowerLab/16SP model ML 795, ADI (ADInstruments), USA)

Results

Figure 6:
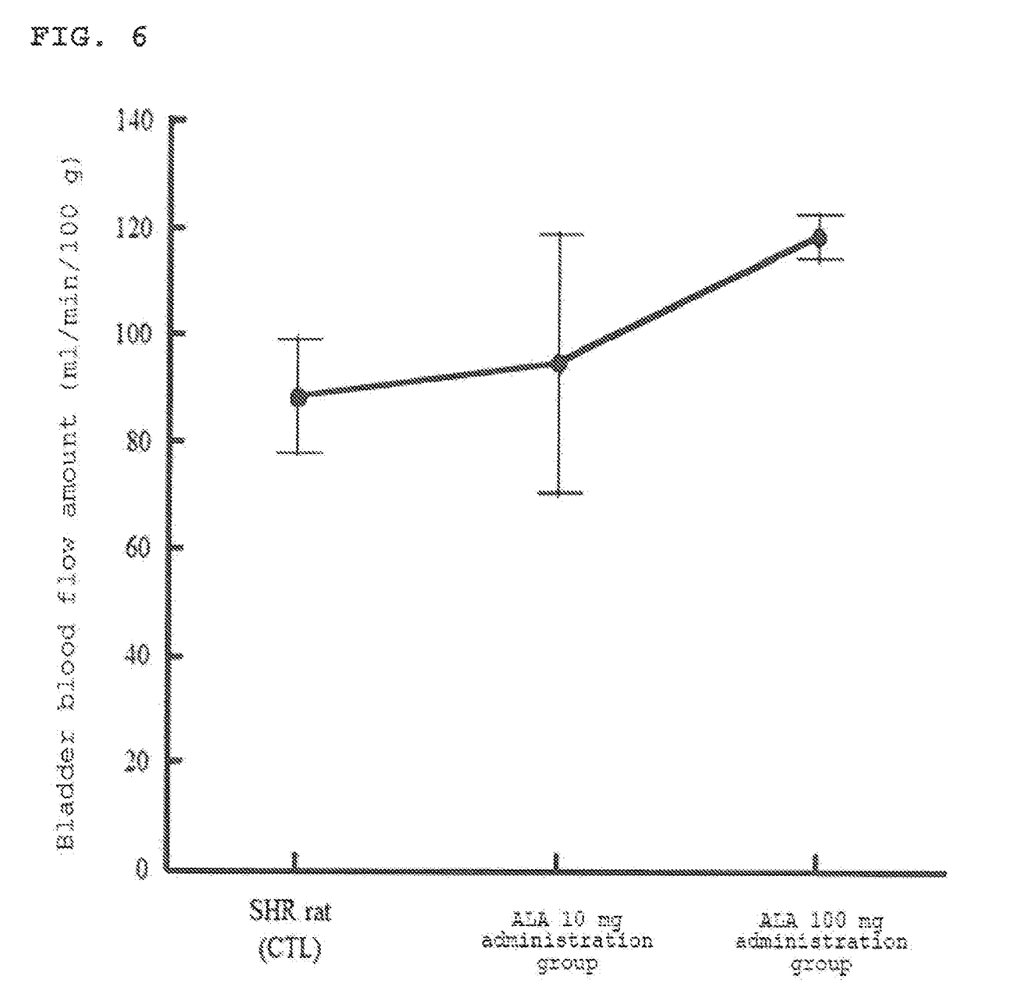
FIG. 6 is a graph that compares the amount of bladder blood flow in the control group and each experimental group.

Results are shown in FIG. 6. In FIG. 6, the vertical axis shows the bladder blood flow amount and the horizontal axis shows each experimental group. As apparent from FIG. 6, a tendency of bladder blood flow to increase ALA dosage-dependently by ALA administration was confirmed. Combined with the results shown in FIGS. 4 and 5, it can be said that the bladder that had contracted due to overactive bladder was expanded due to increase in bladder blood flow. As a result, improvement of overactive bladder by ALA administration was confirmed.

Example 4 (Verification of Mechanism of Improving Overactive Bladder by Ala Administration)

In order to verify the mechanism of improving overactive bladder by ALA administration verified by the above Example in further detail, the relationship between ALA administration and bladder vascular endothelial dysfunction/oxidative stress was investigated. VEGF (Vascular Endothelial Growth Factor) was employed as the marker of the subject's bladder vascular endothelial dysfunction, and MDA (Malondialdehyde), NGF (Nerve Growth Factor), and Nrf2 (Nuclear Respiratory Factor 2) were employed as oxidative stress markers.

1. Measurement of VEGF

ALA administration to a subject and the change in the amount of VEGF expression was investigated. VEGF is a vascular endothelial growth factor, and is used as a marker of bladder vascular endothelial dysfunction.

Preparation of Experimental Group

Preparation of the experimental and control groups was carried out with the method and conditions similar to the method described in Example 1.

Preparation of Rat Bladder Tissue Sample

The bladder tissue of experimental and control groups were processed with the procedure below, and used as samples.
1. Wash 100 mg of tissue with 1×PAS.
2. Homogenize with 500 µl of 1×PBS.
3. Store overnight at −20° C.
4. Carry out freeze-thawing to destroy cell membrane, and centrifuge at 5000 G for 5 min at 4° C.
5. Dispense and store at −20° C. or −80° C.
6. After thawing, centrifuge again and employ for assay.

Measurement of VEGF

ELISA assay was performed with Rat VEGF ELISA kit (CUSABIO CSB-E04757r) according to the protocol provided by the manufacturer.

Results

Figure 7:
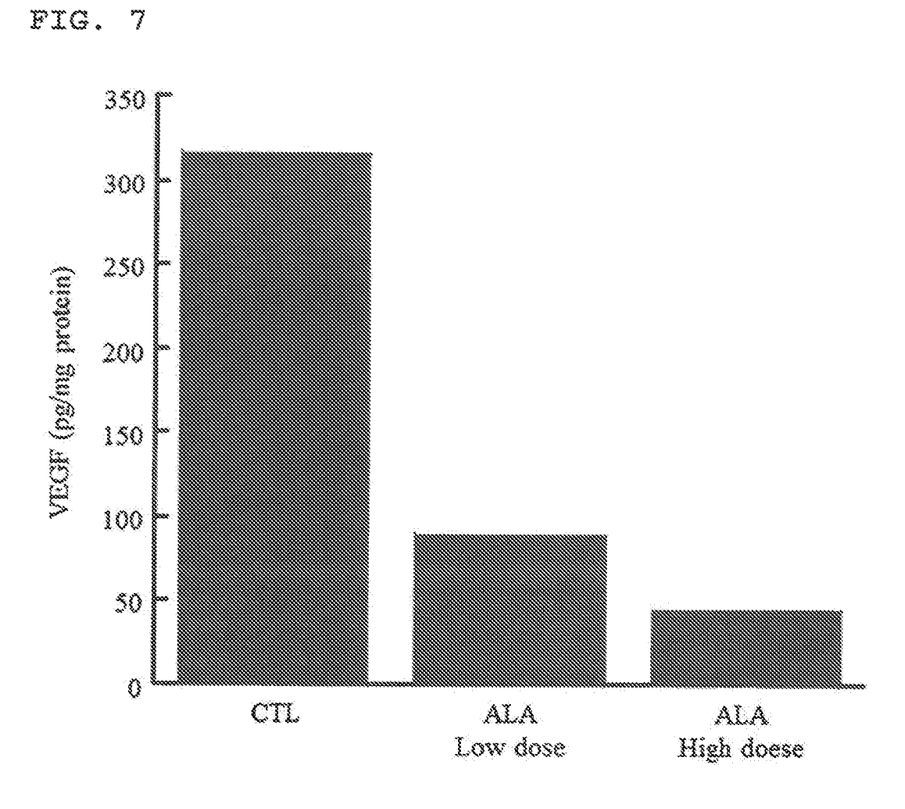
FIG. 7 is a graph that compares the amount of VEGF expression in the bladder tissue of the control group and each experimental group.

Measurement results are shown in FIG. 7. As shown in FIG. 7, the amount of VEGF expression in bladder tissue was significantly reduced in the experimental group (ALA administration group) compared to the control group.

2. Measurement of MDA

ALA administration to a subject and the change in the amount of MDA expression was investigated. MDA is one of lipid peroxidative degradation products, and is known as a major marker of lipid peroxidation.

Preparation of Experimental Group

Preparation of the experimental and control groups was carried out with the method and conditions similar to the method described in Example 1.

Preparation of Rat Bladder Tissue Sample

The bladder tissue of experimental and control groups were processed with the procedure below, and used as samples.
1. Subject to biomasher with 400 µl of cold assay buffer.
2. Centrifuge at 15000 rpm for 5 min at 4° C. After centrifugation, add 300 µl of buffer to the supernatant and store on ice.
3. Correct with protein concentration.

Measurement of MDA

ELISA assay was performed with Malondialdehyde Assay kit (NWK-MDA01) according to the protocol provided by the manufacturer.

Results

Figure 8:
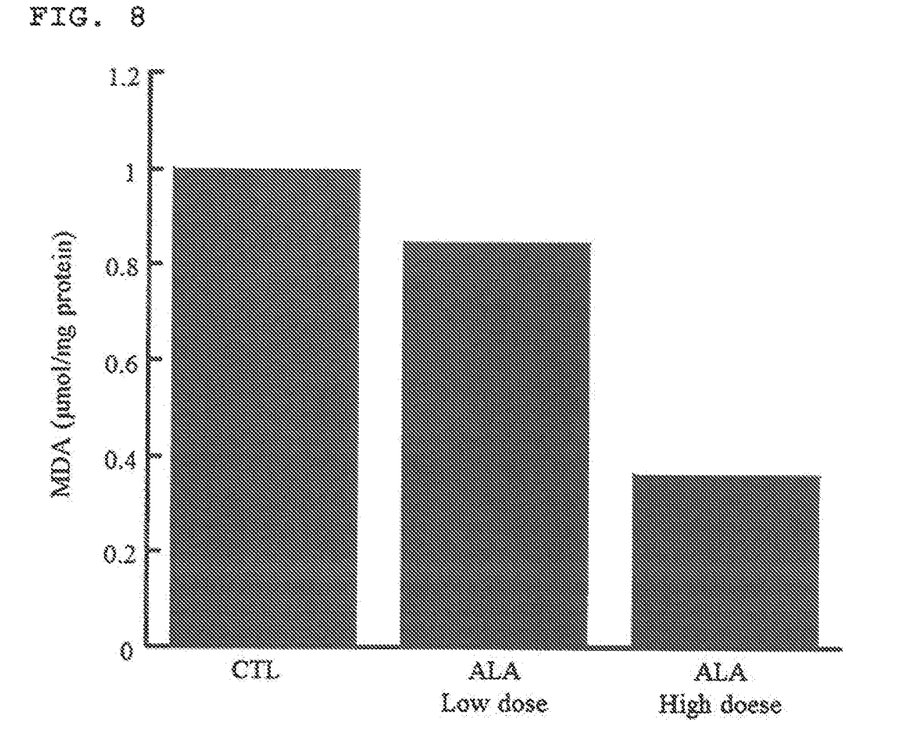
FIG. 8 is a graph that compares the amount of MDA expression in the bladder tissue of the control group and each experimental group.

Measurement results are shown in FIG. 8. As shown in FIG. 8, the amount of MDA expression in bladder tissue was significantly reduced in the experimental group (ALA administration group) compared to the control group.

3. Measurement of NGF

ALA administration to a subject and the change in the amount of NGF expression was investigated. Since micturition reflex is enhanced when NGF increases in the bladder thus resulting in overactive bladder, NGF is employed as a lower urinary tract dysfunction marker.

Preparation of Experimental Group

Preparation of the experimental and control groups was carried out with the method and conditions similar to the method described in Example 1.

Preparation of Rat Bladder Tissue Sample

The bladder tissue of experimental and control groups were processed with the procedure below, and used as samples.
1. Wash 100 mg of tissue with 1×PBS.
2. Homogenize with 1 ml of 1×PBS.
3. Store overnight at −20° C.
4. Carry out freeze-thawing to destroy cell membrane, and centrifuge at 5000 G for 5 min at 4° C.
5. Dispense and store at −20° C. or −80° C.
6. After thawing, centrifuge again and employ for assay.

Measurement of NGF

ELISA assay was performed with Rat NGF ELISA kit (CUSABIO CSB-E24685r) according to the protocol provided by the manufacturer.

Results

Figure 9:
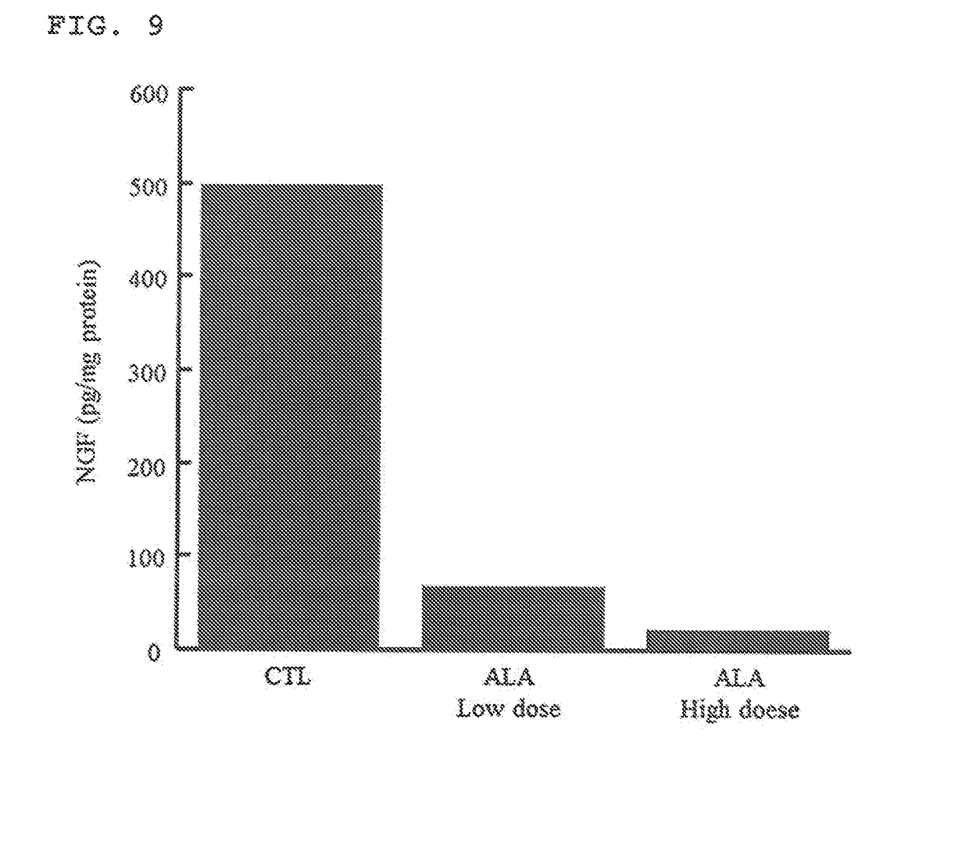
FIG. 9 is a graph that compares the amount of NGF expression in the bladder tissue of the control group and each experimental group.

Measurement results are shown in FIG. 9. As shown in FIG. 9, the amount of NGF expression in bladder tissue was significantly reduced in the experimental group (ALA administration group) compared to the control group.

4. Measurement of Nrf2

ALA administration to a subject and the change in the amount of Nrf2 expression was investigated. Nrf2 is one of transcription factors that regulate the expression of antioxidant enzymes or detoxication metabolism enzymes to control oxidative stress, and is employed as an oxidative stress marker.

Preparation of Experimental Group

Preparation of the experimental and control groups was carried out with the method and conditions similar to the method described in Example 1.

Preparation of Rat Bladder Tissue Sample

The bladder tissue of experimental and control groups were processed with the procedure below, and used as samples.
1. Wash excess blood with PBS.
2. Measure weight.
3. Place 600 µl of PBS on ice in a biomasher to finely mince tissue.
4. Perform ultrasonic wave treatment or freeze-thawing (−20° C./room temperature) 3 times.
5. Centrifuge at 5000 G for 5 minutes.
6. Move the supernatant to a new tube (measure protein concentration).

Measurement of Nrf2

ELISA assay was performed with Rat NFE2L2/NRF2 ELISA kit (LSBio LS-F12145) according to the protocol provided by the manufacturer.

Results

Figure 10:
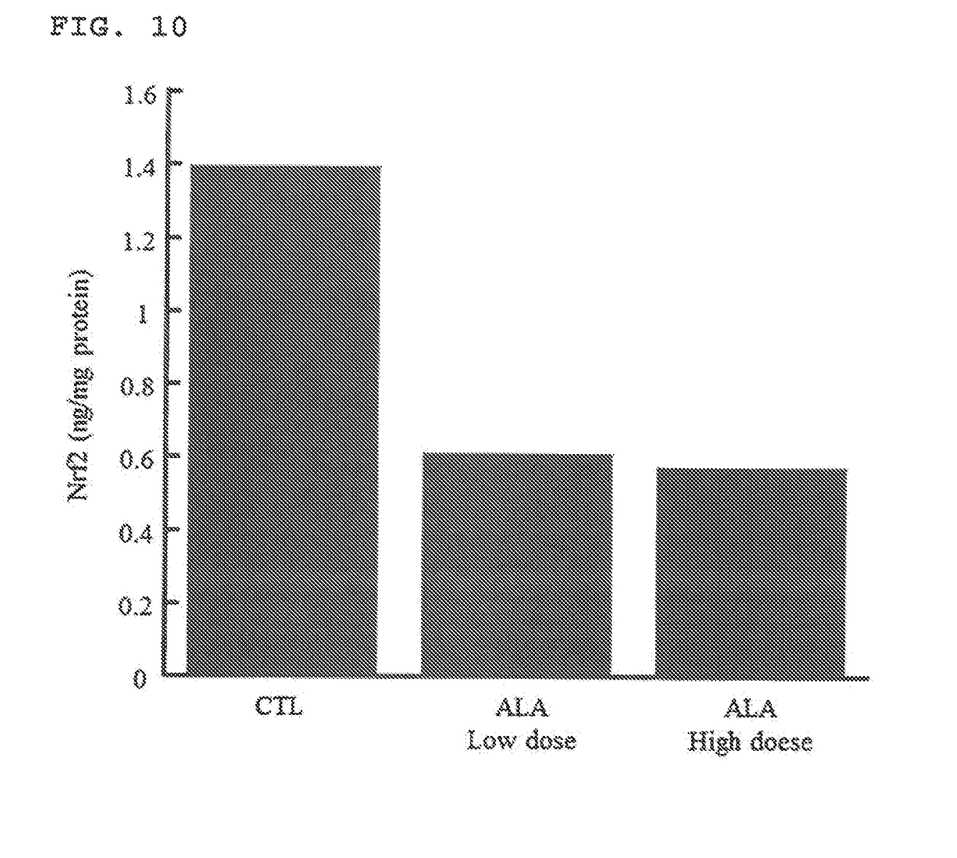
FIG. 10 is a graph that compares the amount of Nrf2 expression in the bladder tissue of the control group and each experimental group.

Measurement results are shown in FIG. 10. As shown in FIG. 10, the amount of Nrf2 expression in bladder tissue was significantly reduced in the experimental group (ALA administration group) compared to the control group.

CONCLUSION

As seen in the results above, the amounts of VEGF, MDA, NGF, and Nrf2 expression were significantly reduced in rat bladder tissue with ALA administration compared to the control group. Since VEGF is related to bladder vascular endothelial dysfunction and MDA, NGF, and Nrf2 are related to oxidative stress of tissue, a mechanism was suggested that as a result of bladder blood flow improvement by ALA administration, tissue disorder or oxidative stress of bladder tissue is alleviated and detrusor muscle overactivity is suppressed.

The invention claimed is:

1. A method for preventing or treating overactive bladder comprising a step of administering to a subject a therapeutically effective amount of the compound of Formula (I):

$$R^1\text{—NHCH}_2\text{COCH}_2\text{CH}_2\text{COOR}^2 \quad (I)$$

wherein $R^1$ represents a hydrogen atom or an acyl group, and $R^2$ represents a hydrogen atom, a linear or branched alkyl group, a cycloalkyl group, an aryl group, or an aralkyl group, or a salt thereof, wherein the therapeutically effective amount of the compound of Formula (I) and/or the salt thereof prevents an overactive bladder in the subject or treats an overactive bladder in the subject.

2. The method of claim 1, wherein the therapeutically effective amount of the compound of Formula (I) is administered in a pharmaceutical composition.

3. The method of claim 2, wherein said overactive bladder is an overactive bladder showing a symptom of frequent urination.

4. The method of claim 2, wherein in the compound of Formula (I),
$R^1$ is selected from the group consisting of a hydrogen atom, an alkanoyl group having 1-8 carbons, and an aroyl group having 7-14 carbons, and
$R^2$ is selected from the group consisting of a hydrogen atom, a linear or branched alkyl group having 1-8 carbons, a cycloalkyl group having 3-8 carbons, an aryl group having 6-14 carbons, and an aralkyl group having 7-15 carbons.

5. The method of claim 2, wherein in the compound of Formula (I), $R^1$ and $R^2$ are hydrogen atoms.

6. The method of claim 2, wherein the pharmaceutical composition further comprises one or more metal-containing compounds.

7. The method of claim 6, wherein the one or more metal-containing compounds comprise a compound containing iron, magnesium, zinc, nickel, vanadium, copper, chromium, molybdenum, or cobalt.

8. The method of claim 6, wherein the one or more metal-containing compounds comprise a compound containing iron, magnesium, or zinc.

9. The method of claim 6, wherein the one or more metal-containing compounds comprise a compound containing iron.

10. The method of claim 9, wherein the compound containing iron comprises sodium ferrous citrate.

11. A method of using the compound of Formula (I):

$$R^1\text{—NHCH}_2\text{COCH}_2\text{CH}_2\text{COOR}^2 \quad (I)$$

wherein $R^1$ represents a hydrogen atom or an acyl group, and $R^2$ represents a hydrogen atom, a linear or branched alkyl group, a cycloalkyl group, an aryl group, or an aralkyl group, or a salt thereof, comprising administering the compound of Formula (I) or the salt thereof to a subject having an overactive bladder.

* * * * *